US006961454B2

(12) United States Patent
Jolly

(10) Patent No.: US 6,961,454 B2
(45) Date of Patent: Nov. 1, 2005

(54) SYSTEM AND METHOD FOR SEGMENTING THE LEFT VENTRICLE IN A CARDIAC MR IMAGE

(75) Inventor: Marie-Pierre Jolly, Hillsborough, NJ (US)

(73) Assignee: Siemens Corporation Research, Inc., Princeton, NJ (US)

( * ) Notice: Subject to any disclaimer, the term of this patent is extended or adjusted under 35 U.S.C. 154(b) by 881 days.

(21) Appl. No.: 09/970,552

(22) Filed: Oct. 4, 2001

(65) Prior Publication Data

US 2003/0069494 A1 Apr. 10, 2003

(51) Int. Cl.[7] .............................................. G06K 9/00
(52) U.S. Cl. ...................................................... 382/131
(58) Field of Search ................................ 382/128, 131, 382/132; 378/4, 21, 25; 600/425; 250/363.04

(56) References Cited

U.S. PATENT DOCUMENTS

| 5,457,754 | A | | 10/1995 | Han et al. ................... 382/128 |
| 5,768,413 | A | * | 6/1998 | Levin et al. ................ 382/173 |
| 6,708,055 | B2 | * | 3/2004 | Geiser et al. ............... 600/425 |
| 6,757,423 | B1 | * | 6/2004 | Amini ........................ 382/154 |

FOREIGN PATENT DOCUMENTS

WO  WO 00/64344  11/2000  ........... A61B/5/055

OTHER PUBLICATIONS

U.S. Appl. No. 09/741,580, filed Dec. 20, 2000 entitled "Method for Learning=Based Object Detection in Cardiac Magnetic Resonance Images".
Marie–Pierre Jolly et al., "Segmentation of the Left Ventricle in Cardiac MR Images", Proc. ICCU, Vancouver, Canada 2001.
Duta et al., "Learning–Based Object Detection in Cardiac MR Images", Proc. IEEE, Corfu, Greece, 1999, pp. 1210–1216.
Geiger et al., "Dynamic Programming for Detecting, Tracking, and Matching Deformable Contours", IEEE Transactions on Pattern Analysis and Machine Intelligence, vol. 17, No. 3, Mar. 1995.
Fleagle et al., "Automated Identification of Left Ventricular Borders from Spin=Echo Magnetic Resonance Images", Investigative Radiology, Apr. 1991, vol. 26, pp. 295–303.
Goshtasby et al., "Segmentation of Cardiac Cine MR Images for Extraction of Right and Left Ventricular Chambers", IEEE Transactions on Medical Imaging, vol. 14, No. 1, Mar. 1995, pp. 56–64.
Weng et al., "Learning–Based Ventricle Detection from Cardiac MR and CT Images", IEEE Transactions on Medical Imaging, vol. 16, No. 4, Aug. 1997, pp. 378–391.
Ramsey et al., "Curve Registration", J.R. Statistical Society, 1998, 60, Part 2, pp. 351–363.
Mortensen et al., "Interactive Segmentation with Intelligent Scissors", Graphical Models and Imaging Processing 60, 1998, pp. 349–384.
Xu et al., "On the Relationship between Parametric and Geometric Active Contours", Proc. 34th Asilomar Conference on Signals, Systems, and Computers, 2000, pp. 483–489.

* cited by examiner

*Primary Examiner*—Andrew W. Johns
*Assistant Examiner*—Shervin Nakhjavan
(74) *Attorney, Agent, or Firm*—Donald B. Paschburg; F. Chau & Associates

(57) ABSTRACT

A method is provided for segmenting a magnetic resonance image of interest of a left ventricle. The method includes determining a myocardium contour according to a graph cut of candidate endocardium contours, and a spline fitting to candidate epicardium contours in the absence of shape propagation. The method further includes applying a plurality of shape constraints to candidate endocardium contours and candidate epicardium contours to determine the myocardium contour, wherein a template is determined by shape propagation of a plurality of magnetic resonance images in a sequence including the magnetic resonance image of interest in the presence of shape propagation.

21 Claims, 4 Drawing Sheets

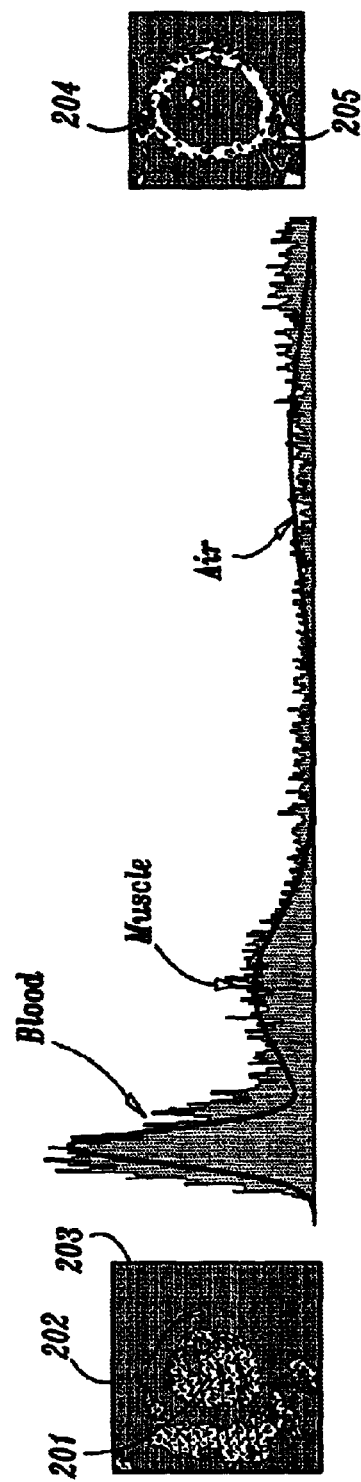

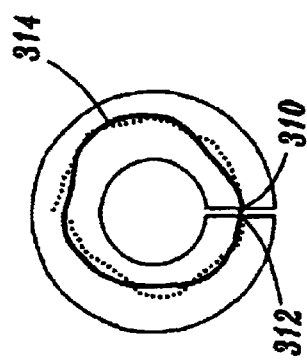
FIG. 3a
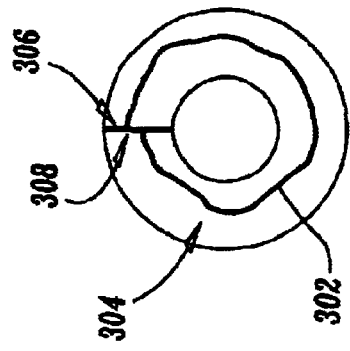
FIG. 3b
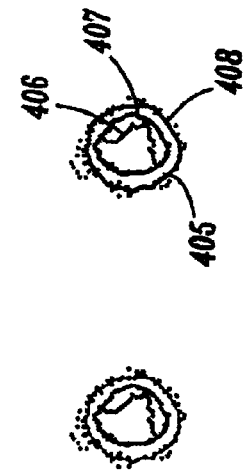
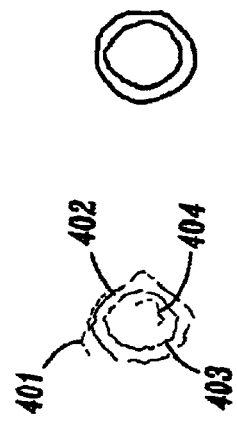
FIG. 4a  FIG. 4b  FIG. 4c  FIG. 4d  FIG. 4e  FIG. 4f

SYSTEM AND METHOD FOR SEGMENTING THE LEFT VENTRICLE IN A CARDIAC MR IMAGE

BACKGROUND OF THE INVENTION

1. Field of the Invention

The present invention relates to medical imaging, and more particularly to extracting the myocardium from four-dimensional MR data (two-dimensional images over time and space).

2. Discussion of Prior Art

Cardiovascular disease is the leading cause of death in the United States. Mortality has been declining over the years as lifestyle has changed, but the decline is also due to the development of new technologies to diagnose disease. One of these techniques is magnetic resonance imaging (MRI), which provides time-varying three-dimensional imagery of the heart. To help in the diagnosis of disease, physicians are interested in identifying heart chambers, the endocardium and epicardium, and measuring changes in ventricular blood volume (ejection fraction) and wall thickening properties over a cardiac cycle. The left ventricle is of particular interest since it pumps oxygenated blood out to distant tissue in the entire body.

There has been a large amount of research on the analysis of medical images. Segmentation of these images has been particularly challenging. In the early nineties, researchers realized that tracking the cardiac wall motion in MR images could be used to characterize meaningful functional changes. A system proposed by S. R. Fleagle, D. R. Thedens, J. C. Ehrhardt, T. D. Scholz, and D. J. Skorton, "Automated identification of left ventricular borders from spin-echo resonance images", *Investigative Radiology*, 26:295–303, 1991, delineates the border of the myocardium using a minimum cost path graph search method after a user indicates the center of the left ventricular cavity and an area of interest, for example, with a mouse. D. Geiger, A. Gupta, L. A. Costa, and J. Vlontzos, "Dynamic programming for detecting, tracking, and matching deformable contours", *IEEE Trans. PAMI*, 17(3):294–302, 1995, used a dynamic programming approach to refine the contours specified by the user. A. Goshtasby and D. A. Turner, "Segmentation of cardiac cine MR images for extraction of right and left ventricular chambers", *IEEE Trans. Medical Imaging*, 14(1):56–64,1995, proposed a two step method combining intensity thresholding to recover blood from an image and a local gradient to outline strong edges using elastic curves. J. Weng, A. Singh, and M. Y. Chiu, "Learning-based ventricle detection from cardiac MR and CT images", *IEEE Trans. Medical Imaging*, 16(4):378–391, 1997, applied a threshold to an image based on parameters estimated during a learning phase to approximate the segmentation.

However, no known system or method exists for providing an adaptive technique of analyzing cardiac images. Therefore, a need exists for a method of cardiac segmentation combining edge, region and shape information in a deformable template.

SUMMARY OF THE INVENTION

According to an embodiment of the present invention, a method is provided for segmenting a magnetic resonance image of interest of a left ventricle. The method includes determining a myocardium contour according to a graph cut of candidate endocardium contours, and a spline fitting to candidate epicardium contours in the absence of shape propagation. The method further includes applying a plurality of shape constraints to candidate endocardium contours and candidate epicardium contours to determine the myocardium contour, wherein a template is determined by shape propagation of a plurality of magnetic resonance images in a sequence including the magnetic resonance image of interest.

According to an embodiment of the present invention, a method for segmenting a magnetic resonance image of interest of a left ventricle includes determining a myocardium response image according to a histogram of pixel intensity in magnetic resonance image of interest. The method includes determining a plurality of candidate contours, according to a plurality of energy functions, to which a plurality of confidence values are assigned. The method further includes applying a plurality of shape constraints to the candidate endocardium contours and the candidate epicardium contours to determine a myocardium contour.

The myocardium contour is based on a plurality of magnetic resonance images in a sequence including the magnetic resonance image of interest, wherein the myocardium contour includes an endocardium contour and an epicardium contour.

The method determines an approximate contour pair of the left ventricle according to a plurality of points defined in a gray level profile of the image as an intersection of a plurality of cross sections of the left ventricle. The approximate contour pair is determined according to a Hough transform array to vote for a center position and a radius of a myocardium centerline.

Determining the myocardium response image according to the histogram of pixel intensity further includes fitting a mixture of Gaussians to the histogram of pixel intensity to determine portions of blood, muscle and air in the image.

For each candidate closed contour, the method further includes defining a search space around an approximate contour, defining a line of source nodes and sink nodes, and determining a shortest path between the source nodes and the sink nodes. The method includes defining a new source node and a plurality of new sink nodes, and determining a shortest path between the new source node and new sink nodes.

The candidate endocardium contours and the candidate epicardium contours are each determined according to a combination of a gradient magnitude and a direction using a cross product of a gradient direction and a contour direction. The method further includes determining a first candidate endocardium contour according to a positive cross product of a gradient direction in the input image and a contour direction, and determining a second candidate endocardium contour according to a negative cross product of a gradient direction in the myocardium image and a contour direction. The method includes determining a first candidate epicardium contour according to a gradient magnitude in the input image, and determining a second candidate epicardium contour according to a positive cross product of a gradient direction in the myocardium image and a contour direction.

The method determines a one-to-one match matrix, wherein points on the endocardium contour and epicardium contour are assigned to a plurality of template points, wherein the template points are determined from propagation through a plurality of magnetic resonance images.

According to an embodiment of the present invention, a method is provided for segmenting a magnetic resonance image of interest of a left ventricle. The method includes determining a myocardium response image according to a histogram of pixel intensity in magnetic resonance image of interest, determining a plurality of candidate contours, according to a plurality of energy functions, to which a plurality of confidence values are assigned. The method further includes determining a myocardium contour according to a graph cut of candidate endocardium contours, and a spline fitting to candidate epicardium contours in the absence of shape propagation. The method applies a plurality of shape constraints to the candidate endocardium contours and the candidate epicardium contours, to determine the myocardium contour, wherein a template is determined by shape propagation of a plurality of magnetic resonance images in a sequence including the magnetic resonance image of interest.

The myocardium contour includes an endocardium contour and an epicardium contour.

The method determines an approximate contour pair of the left ventricle according to a plurality of points defined in a gray level profile of the image as an intersection of a plurality of cross sections of the left ventricle, wherein the contour pair comprises an endocardium contour and an epicardium contour. The approximate contour pair is determined according to a Hough transform array to vote for a center position and a radius of a myocardium centerline.

Determining the myocardium response image according to the histogram of pixel intensity further comprises fitting a mixture of Gaussians to the histogram of pixel intensity to determine portions of blood, muscle and air in the image.

For each candidate closed contour, the method further comprises defining a search space around the myocardium response image, defining a line of source nodes and sink nodes, and determining a shortest path between the source nodes and the sink nodes. The method includes defining a new source node and a plurality of new sink nodes, and determining a shortest path between the new source node and new sink nodes.

The candidate endocardium contours and the candidate epicardium contours are each determined according to a combination of a gradient magnitude and a direction using a cross product of a gradient direction and a contour direction. The method further comprises determining a first candidate endocardium contour according to a positive cross product of a gradient direction in the input image and a contour direction, and determining a second candidate endocardium contour according to a negative cross product of a gradient direction in the myocardium image and a contour direction. The method includes determining a first candidate epicardium contour according to a gradient magnitude in the input image, and determining a second candidate epicardium contour according to a positive cross product of a gradient direction in the myocardium image and a contour direction.

The graph cut further includes defining a graph wherein each node corresponds to a connected component region between candidate pixels on the candidate contours, and determining a minimum cut between a center node and an outside node.

The spline fitting further includes fitting a spline through points of the candidate contours.

According to an embodiment of the present invention, a program storage device is provided readable by machine, tangibly embodying a program of instructions executable by the machine to perform method steps for segmenting a magnetic resonance image of interest of a left ventricle. The method includes determining a myocardium response image according to a histogram of pixel intensity in magnetic resonance image of interest, determining a plurality of candidate contours, according to a plurality of energy functions, to which a plurality of confidence values are assigned. The method further includes determining a myocardium contour according to a graph cut of candidate endocardium contours, and a spline fitting to candidate epicardium contours in the absence of shape propagation. The method applies a plurality of shape constraints to the candidate endocardium contours and the candidate epicardium contours, to determine the myocardium contour, wherein a template is determined by shape propagation of a plurality of magnetic resonance images in a sequence including the magnetic resonance image of interest.

BRIEF DESCRIPTION OF THE DRAWINGS

Preferred embodiments of the present invention will be described below in more detail, with reference to the accompanying drawings:

FIG. 2a a shows an input image according to an embodiment of the present invention;

FIG. 2b shows a histogram of the input image of FIG. 2a, fitted with a mixture of Gaussians according to an embodiment of the present invention;

FIG. 2c shows a myocardium response image according to an embodiment of the present invention;

FIGS. 3a–b show an example of two passes of Dijkstra's method according to an embodiment of the present invention;

FIGS. 4a–f show an example of applying shape constraints to recover the myocardium contours according to an embodiment of the present invention;

DETAILED DESCRIPTION OF PREFERRED EMBODIMENTS

The present invention can be embodied in any suitable commercial cardiac analysis package, such as the ARGUS cardiac analysis package from Siemens, which offers a complete system of drawing tools and automatic segmentation methods to allow the physician to outline the myocardium in each image in the patient data set, determine volumes, ejection fraction, and perform a thickening analysis.

Figure 1:
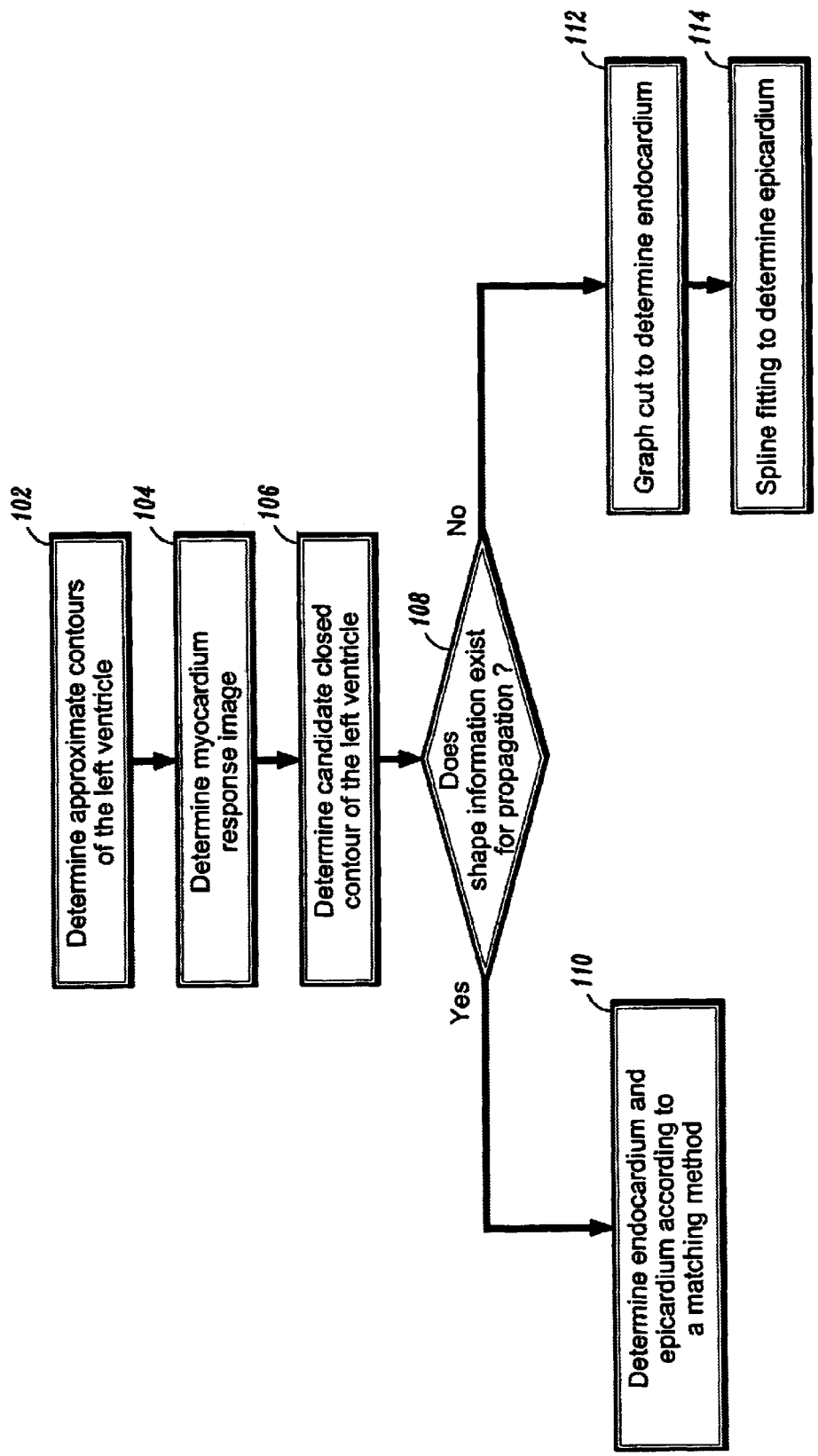
FIG. 1 is a flow chart showing a method of segmentation according to an embodiment of the present invention.

Referring to FIG. 1, illustrating a method according to an embodiment of the present invention, the method determines approximate contours of the left ventricle 102 and a myocardium response image 104 according to a histogram of pixel intensity in the magnetic resonance image of interest. The method determines a plurality of candidate closed contours of the left ventricle 106, according to a plurality of energy functions. Further, the method is aware of whether shape information exists for the magnetic resonance image of interest 108 and is able to apply a desired method to determine a myocardium image. For example, in the presence of shape information, the method determines a template from propagation through a plurality of magnetic resonance images, and determines an endocardium and epicardium according to a matching technique between the candidate contours and the template. The matching technique can include, for example, point-pattern matching and shape matching. The method determines an endocardium contour according to a graph cut 112 and an epicardium contour according to a spline fitting 114 to the candidate contours for a singular image, where a template is not present.

It is to be understood that the present invention may be implemented in various forms of hardware, software, firmware, special purpose processors, or a combination thereof. In one embodiment, the present invention may be implemented in software as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present invention provided herein, one of ordinary skill in the related art will be able to contemplate these and similar implementations or configurations of the present invention.

According to an embodiment of the present invention, a method is provided which automatically hypothesizes two concentric circles at the location of the left ventricle in an MR image. However, due to the relative symmetry of the left ventricle and computational constraints, the method uses the gray values of the pixels along four cross sections through the ventricle instead of the entire region to determine a feature set. A method of automatic localization is described in Ser. No. 09/741,580, entitled, Method for Learning-Based Object Detection in Cardiac Magnetic Resonance Images, and is incorporated by reference herein in its entirety.

The present invention patterns a Markov process. A Markov analysis looks at a sequence of events, and analyzes a tendency of an event to be followed by another event, generating a new sequence of random but related events. According to an embodiment of the present invention, in a learning phase, positive and negative examples are presented and the method finds the ordering of the Markov process that maximizes a separation (minimizes the Kullbach distance, also known as the relative entropy or cross entropy) between the two classes in the training set. The method includes a detection phase, during which a test image is scanned and each location is assigned to a class based on the log-likelihood ratio.

Neighboring positions classified as the left ventricle are portioned into clusters. The method defines eight salient points in the gray level profiles as the intersection of the four cross sections with the ventricle's medical axis. Average profiles are built from training example profiles aligned using a curve registration technique, for example, as proposed by Ramsay and Xi. The cross sections of each of the cluster candidates are warped onto corresponding average profiles. The location of the salient points in the image are then accumulated using a Hough transform array to vote for the most likely center position and radius for the myocardium centerline.

Typically, the user segments one image, for example, the slice closest to the valves at end-diastole (ED base) and propagates the segmented contours to all the slices in the ED phase (ED propagation). The ED contours can be propagated to the end-systole (ES) phase (ES propagation) to compute the ejection fraction. For a more detailed analysis, the user can also propagate all the ED contours to all the images in all the phases using temporal propagation.

For ED propagation, the present invention uses the automatic localization method described above. However, since the ventricle size is approximately known from the template image, the scale search can be limited, for example, to between 0.85 and 1.15 times the size of the template. The method can limit the search space for the location of the ventricle, for example, to 30 pixels around the location of the template. For ES propagation, the method knows the location of the left ventricle has not changed and therefore, the template contours can be scaled. The endocardium is scaled by 0.6 and the epicardium by 0.9. In the case of temporal propagation, both the location and scale of the contours do not change significantly. Therefore, the method can copy the contours from one image to the next.

In MR imaging, the intensity of a pixel depends on the properties of the tissue being imaged. As shown in FIG. 2a, in an MR image of the left ventricle, the blood is bright 201, the muscles are somewhat dark 202, but not as dark as the air-filed lungs 203. This fact can be verified by looking at the histogram of a region around the myocardium as shown in FIG. 2b. The method uses an Expectation-Maximization (EM) method to fit a mixture of three Gaussians to the histogram. The method then creates a myocardium response image, showing the probability that a pixel belongs to the middle Gaussian which corresponds to the myocardium. It can be seen from FIG. 2c that the left ventricle myocardium 204 is highlighted, but neighboring organs, e.g., 205, are also highlighted.

To complement the results of region segmentation, the method uses an active contour formulation similar to Geiger's dynamic programming approach or Mortensen and Barrett's Dijkstra's approach. The advantage of these graph theoretic methods over a gradient descent approach as proposed by Kass et al. is that they are able to recover the global optimum of the energy function and are therefore insensitive to the initial contour position.

Geiger defines the energy of a contour $(p_1 \ldots p_n)$ as:

$$E(p_1 \ldots p_n) = \sum_{i=1}^{n} \frac{1}{\|\nabla I(p_i)\| + \varepsilon} + \alpha \sum_{i=2}^{n} |\vec{\nabla} I(p_i) - \vec{\nabla} I(p_{i-1})| \quad (1)$$

where $\|\nabla I(p)\|$ is the magnitude and $\vec{\nabla} I(p)$ is the direction of the image gradient at pixel p. This is equivalent to finding a shortest path in a graph where nodes correspond to pixels and the cost of a link between two neighboring pixels is defined as:

$$e(p_1, p_2) = \frac{1}{\|\vec{\nabla} I(p_2)\| + \varepsilon} + \alpha |\vec{\nabla} I(p_2) - \vec{\nabla} I(p_1)| \qquad (2)$$

Given an approximate contour in an image, the method places a symmetrical search space 304 around it and defines a line of source nodes 306, connected to a "pseudo" source node, and sink nodes 308. Dijkstra's method then finds the shortest path between the pseudo source node and one of the sink nodes 302. The method defines a new single source point 312 in the middle of the recovered contour and a set of sink nodes 310 neighboring the source node, and does a second pass of Dijkstra's method to produce a closed contour 314.

To combine the information provided by both the image and the myocardium response image, Dijkstra's method is implemented with two different energy functions. Each run gives different candidate points for the contours, along with a confidence based on the contribution of each point to the total energy function. One energy function combines gradient magnitude and direction using the cross product of the gradient direction and the contour direction. In this case, the contour is built clockwise by Dijkstra process and the image gradient points from bright to dark. To separate a bright region inside from a dark region outside, resp. a dark region inside from a bright region outside, the z component of the cross product between the image gradient and the contour direction should be positive, resp. negative. The energy is set to a large number otherwise. The cost of a link between two pixels is:

$$e(I, z > 0, p_1, p_2) = \begin{cases} \frac{1}{\|\vec{\nabla} I(p_2)\|^2 + \varepsilon} & \text{if } z = \begin{array}{l}(x_2 - x_1)\sin(\vec{\nabla} I(p_2)) - \\ (y_2 - y_1)\cos(\vec{\nabla} I(p_2))\end{array} > 0 \\ 1/\varepsilon & \text{otherwise} \end{cases} \qquad (3)$$

where $\varepsilon$ is a small constant, for example, 0.001, to bound the energy function. E(I,z>0) and E(H,z<0) can be used for the endocardium, where I is the input image and H is the myocardium response image. For epicardium, E(H,z>0) can be used. Since the gradient direction in I outside the myocardium flips between the bright right ventricle and the dark lungs, E'(I) can be used, which can be defined as:

$$e'(I, p_1, p_2) = \frac{1}{\|\vec{\nabla} I(p_2)\|^2 + \varepsilon} \qquad (4)$$

Different energy functions highlight different features of the myocardium.

Dijktra's method is applied with various energy functions and all points on the resulting contours are candidate points for the final contour. When the contours are propagated from one image to the next, either spatially or temporally, it is reasonable to assume that the shape of the contours does not change drastically. Based on this assumption, the method can determine which parts of which contours are correct.

A shape alignment method, for example, as proposed by Duta et al., is used to establish a correspondence between a subset A' of the template points $A=\{A_j\}_{j=1,\ldots,a}$ and a subset B' of the candidate test points $B=\{B_k\}_{k=1,\ldots,b}$. According to an embodiment of the present invention, both contours are considered as one shape. Given a pair of "corresponding" points in A and B, a rigid similarity transform is hypothesized to align the contours. A one-to-one match matrix M is determined to assign every point B to its closest neighbor in A if the distance is less than a threshold. This allows the following equation:

$$f(M) = \frac{1}{n^2} \sum_{j=1}^{n} w_j \left[ (x_{A_j} - ax_{B_j} + cy_{B_j} - b)^2 + (y_{A_j} - ay_{B_j} + cx_{B_j} - d)^2 \right] + \frac{2}{n} \qquad (5)$$

where n is the number of correspondences and (a,b,c,d) are the parameters of the similarity transform. The weight $w_j$ is set to be the confidence of the test point $B_j$. The goal is to minimize f(M). It is not possible to evaluate all possible quadruplets of points, so the 10% of the points with the largest confidence in the test set are chosen and paired with points from the same contour in the template set. One of ordinary skill in the art would recognize in light of the present invention that larger and smaller sets of points can be chosen.

FIG. 4a shows the input image and FIG. 4b illustrates four recovered contours, 401–404, where darker points show higher confidence. FIG. 4c shows the template shape from the segmentation of the previous image. FIG. 4d shows the established correspondences for the best similarity transform. The shape constraints allow the method to choose the outside candidate points for the endocardium 407 rather than the inside points that outline the papillary muscles 406, and the inside candidate points for the epicardium 405 rather than the outside points that outlined the fat 408. Once the correspondences are established, the template shape is warped by moving the template points to their corresponding test points as in FIG. 4e. The contours are smoothed using the method proposed by Xu et al., which minimizes shrinkage. A final segmentation result is shown in FIG. 4f.

When an image needs to be segmented on its own, not in the context of propagation, there is no shape information available to the system. The endocardium should be pushed as far as possible away from the center so that it outlines the myocardium rather than the papillary muscles, and the epicardium should stay close the endocardium. To enforce these constraints, the method modifies the confidence values in the following way:

$$C_{endo}(p) = C_{endo}(p) \left( \frac{d(p, \Omega)}{\max_p d(p, \Omega)} \right)^3$$

$$C_{epi}(p) = C_{epi}(p) \left( \frac{d(p, endo)}{\max_p d(p, endo)} \right)^3$$

where $\Omega$ is the center of mass of the confidence points.

Figure 5A:
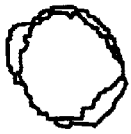
FIGS. 5a–d show an example of a graph cut method according to an embodiment of the present invention.
Figure 5B:
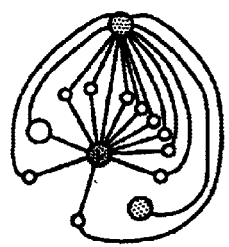
Figure 5C:
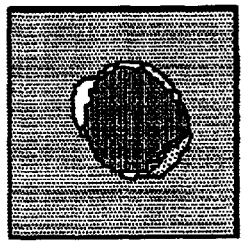
Figure 5D:
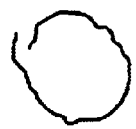

For the endocardium, the method determines the cycle with a maximum confidence. FIG. 5a shows an example of a confidence image. A graph, for example, as illustrated in FIG. 5c, is defined where each node corresponds to connected component regions, as shown in FIG. 5b, between confidence pixels on the candidate contours. The weight of an edge between two nodes is inversely proportional to the confidence of pixels on the common boundary. Then, the method determines a minimum cut between the center node and the outside node. A max flow method is used to determine the minimum cut. FIG. 5d shows an example of a final segmentation, or myocardium contour (shown in dark).

For the epicardium, the method needs a smooth contour since there is no clear edge between the myocardium and the liver, and the right ventricle myocardium appears to merge into the left ventricle myocardium. Therefore, the method fits a spline to the points of the two candidate contours. Spline curves originate from flexible strips used to create smooth curves. Like Bezier curves, splines are formed from piecewise approximations of cubic polynomial functions with zero, first and second order continuity. B-Splines are an example of a particular type of spline.

In order to test our algorithm, we have collected 29 patient data sets along with a manual segmentation of the ED and ES phases by radiologists, for a total of 458 segmented images. The images were acquired on Siemens MAGNETOM systems using two different pulse sequences. FLASH pulse sequences were traditionally used for MR cineangiography. Siemens recently pioneered the TrueFISP pulse sequences for cardiac cine imaging which present higher contrast-to-noise ratio without affecting temporal or spatial resolution. We collected 22 TrueFISP patients and 7 FLASH patients. Our database presents a great variety of heart shapes, image contrast, and edge crispness. The difficulty with FLASH images is that the edges can be blurred. The challenge with TrueFISP images is that the papillary muscles are so well defined that it can be difficult to avoid outlining them. Further, the user may not want to outline them and the shape constraint can help in this task.

Figure 6:
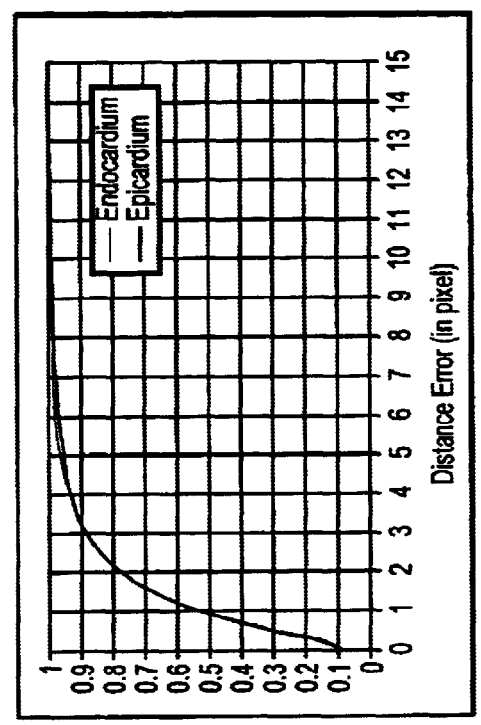
FIG. 6 is a graph showing a cumulative distribution of error distances between true contours and segmented contours, over all points, over all images, and over all patients.

The method automatically segments ED and ES phases of all the datasets. To compare the automatic contours A with the true contours B, the method determines the distances $d(a,B)=\min_{b \in B} \|a-b\|$ for all points a in the automatic contour. The method also determines $d(b,A)$ for all points b in the true contour. FIG. 6 shows the cumulative distribution of these error distances over all ED and ES images of all 29 datasets. It can be seen that, on the average, the error is less than one pixel and an error of five pixels or more is made less than five percent of the time.

The present invention proposes a method for segmenting the left ventricle in cardiac MR images. The method combines edge information, region information obtained from an EM fitting of a mixture of Gaussians to a histogram, and shape information through a point pattern matching strategy. The method can be integrated into, for example, the ARGUS cardiac analysis package from Siemens.

Having described embodiments for cardiac segmentation combining edge, region and shape information in a deformable template, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A method for segmenting a magnetic resonance image of interest of a left ventricle comprising the steps of:

determining a myocardium contour according to a graph cut of candidate endocardium contours, and a spline fitting to candidate epicardium contours in the absence of shape propagation; and applying a plurality of shape constraints to the candidate endocardium contours and the candidate epicardium contours, to determine the myocardium contour, wherein a template is determined by shape propagation of a plurality of magnetic resonance images in a sequence including the magnetic resonance image of interest, in the presence of shape propagation.

2. A method for segmenting a magnetic resonance image of interest of a left ventricle comprising the steps of:

determining a myocardium response image according to a histogram of pixel intensity in magnetic resonance image of interest;

determining a plurality of candidate contours, according to a plurality of energy functions, to which a plurality of confidence values are assigned; and applying a plurality of shape constraints to the candidate endocardium contours and the candidate epicardium contours to determine a myocardium contour.

3. The method of claim 2, wherein the myocardium contour is based on a plurality of magnetic resonance images in a sequence including the magnetic resonance image of interest, wherein the myocardium contour includes an endocardium contour and an epicardium contour.

4. The method of claim 2, further comprising the step of determining an approximate contour pair of the left ventricle according to a plurality of points defined in a gray level profile of the image as an intersection of a plurality of cross sections of the left ventricle.

5. The method of claim 4, wherein the approximate contour pair is determined according to a Hough transform array to vote for a center position and a radius of a myocardium centerline.

6. The method of claim 2, wherein the step of determining the myocardium response image according to the histogram of pixel intensity further comprises the step of fitting a mixture of Gaussians to the histogram of pixel intensity to determine portions of blood, muscle and air in the image.

7. The method of claim 2, wherein for each candidate closed contour, the method further comprises the steps of:

defining a search space around an approximate contour;

defining a line of source nodes and sink nodes;

determining a shortest path between the source nodes and the sink nodes;

defining a new source node and a plurality of new sink nodes; and determining a shortest path between the new source node and new sink nodes.

8. The method of claim 2, wherein the candidate endocardium contours and the candidate epicardium contours are each determined according to a combination of a gradient magnitude and a direction using a cross product of a gradient direction and a contour direction.

9. The method of claim 8, further comprising the steps of:

determining a first candidate endocardium contour according to a positive cross product of a gradient direction in the input image and a contour direction;

determining a second candidate endocardium contour according to a negative cross product of a gradient direction in the myocardium image and a contour direction;

determining a first candidate epicardium contour according to a gradient magnitude in the input image; and determining a second candidate epicardium contour according to a positive cross product of a gradient direction in the myocardium image and a contour direction.

10. The method of claim 2, further comprising the step of determining a one-to-one match matrix, wherein points on the endocardium contour and epicardium contour are assigned to a plurality of template points, wherein the template points are determined from propagation through a plurality of magnetic resonance images.

11. A method for segmenting a magnetic resonance image of interest of a left ventricle comprising the steps of:

determining a myocardium response image according to a histogram of pixel intensity in magnetic resonance image of interest;

determining a plurality of candidate contours, according to a plurality of energy functions, to which a plurality of confidence values are assigned;

determining a myocardium contour according to a graph cut of candidate endocardium contours, and a spline fitting to candidate epicardium contours in the absence of shape propagation; and applying a plurality of shape constraints to the candidate endocardium contours and the candidate epicardium contours to determine the myocardium contour, wherein a template is determined by shape propagation of a plurality of magnetic resonance images in a sequence including the magnetic resonance image of interest, in the presence of shape propagation.

12. The method of claim 11, wherein the myocardium contour includes an endocardium contour and an epicardium contour.

13. The method of claim 11, further comprising the step of determining an approximate contour pair of the left ventricle according to a plurality of points defined in a gray level profile of the image as an intersection of a plurality of cross sections of the left ventricle.

14. The method of claim 13, wherein the approximate contour pair is determined according to a Hough transform array to vote for a center position and a radius of a myocardium centerline.

15. The method of claim 11, wherein the step of determining the myocardium response image according to the histogram of pixel intensity further comprises the step of fitting a mixture of Gaussians to the histogram of pixel intensity to determine portions of blood, muscle and air in the image.

16. The method of claim 11, wherein the closed contour includes a plurality of candidate contours, and for each contour, further comprises the steps of:

defining a search space around an approximate contour;

defining a line of source nodes and sink nodes;

determining a shortest path between the source nodes and the sink nodes;

defining a new source node and a plurality of new sink nodes; and determining a shortest path between the new source node and new sink nodes.

17. The method of claim 11, wherein the candidate endocardium contour and the candidate epicardium contour are each determined according to a combination of a gradient magnitude and a direction using a cross product of a gradient direction and a contour direction.

18. The method of claim 17, further comprising the steps of:

determining a first candidate endocardium contour according to a positive cross product of a gradient direction in the input image and a contour direction;

determining a second candidate endocardium contour according to a negative cross product of a gradient direction in the myocardium image and a contour direction;

determining a first candidate epicardium contour according to a gradient magnitude in the input image; and determining a second candidate epicardium contour according to a positive cross product of a gradient direction in the myocardium image and a contour direction.

19. The method of claim 11, wherein the graph cut further includes the steps of:

defining a graph wherein each node corresponds to a connected component region between confidence pixels on the candidate contours; and determining a minimum cut between a center node and an outside node.

20. The method of claim 11, wherein the spline fitting further includes the step of fitting a spline through points of the candidate contours.

21. A program storage device readable by machine, tangibly embodying a program of instructions executable by the machine to perform method steps for segmenting a magnetic resonance image of interest of a left ventricle, the method steps comprising:

determining a myocardium response image according to a histogram of pixel intensity in magnetic resonance image of interest;

determining a plurality of candidate contours, according to a plurality of energy functions, to which a plurality of confidence values are assigned;

determining a myocardium contour according to a graph cut of candidate endocardium contours, and a spline fitting to candidate epicardium contours in the absence of shape propagation; and applying a plurality of shape constraints to the candidate endocardium contour and the candidate epicardium contours to determine the myocardium contour, wherein a template is determined by shape propagation of a plurality of magnetic resonance images in a sequence including the magnetic resonance image of interest, in the presence of shape propagation.

* * * * *